United States Patent
Kuniyoshi et al.

(10) Patent No.: US 7,871,596 B2
(45) Date of Patent: Jan. 18, 2011

(54) HIGHER FATTY ACID TRIESTER COMPOUND HAVING DIETHYLENETRIAMINE-TYPE METAL CHELATE STRUCTURE

(75) Inventors: Hidenobu Kuniyoshi, Kanagawa (JP); Kazuhiro Aikawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 425 days.

(21) Appl. No.: 12/126,018

(22) Filed: May 23, 2008

(65) Prior Publication Data

US 2008/0299043 A1 Dec. 4, 2008

(30) Foreign Application Priority Data

Jun. 1, 2007 (JP) ............................. 2007-146410

(51) Int. Cl.
*A61K 49/00* (2006.01)
(52) U.S. Cl. ............................. 424/9.1; 424/450; 534/16
(58) Field of Classification Search ................. 424/9.1, 424/450; 534/16
See application file for complete search history.

(56) References Cited

FOREIGN PATENT DOCUMENTS

| JP | 2008-150318 A | 7/2008 |
|----|---------------|--------|
| WO | 97/26921 A2 | 7/1997 |
| WO | 2007/072983 A1 | 6/2007 |

OTHER PUBLICATIONS

Database WPI Week 200750, Thomson Scientific, London, GB; AN 2007-509658. XP002497621.
Extended European Search Report dated Oct. 7, 2008.

*Primary Examiner*—Deborah D Carr
(74) *Attorney, Agent, or Firm*—Sughrue Mion, PLLC

(57) ABSTRACT

A compound having superior solubility and suitable for a liposome contrast medium selective for a lesion such as vascular diseases is provided which is represented by the following general formula (I)

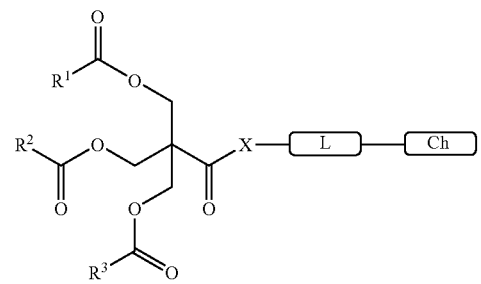

wherein $R^1$, $R^2$ and $R^3$ independently represent an alkyl group or an alkenyl group having 8 to 25 carbon atoms; X represents —O—, or —N(Z)— (Z represents hydrogen atom, or an alkyl group having 1 to 3 carbon atoms); and L represents a divalent bridging group constituted by atoms selected from the group consisting of carbon atom, hydrogen atom, oxygen atom, nitrogen atom and sulfur atom; Ch represents a functional group represented by the following general formula (II), and in the general formula (II), any one of the hydrogen atom $H^a$, $H^b$, $H^c$, $H^d$, $H^e$, and $H^f$ is substituted with L.

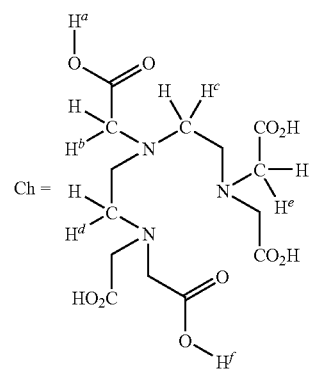

17 Claims, No Drawings

HIGHER FATTY ACID TRIESTER COMPOUND HAVING DIETHYLENETRIAMINE-TYPE METAL CHELATE STRUCTURE

CROSS-REFERENCE TO RELATED APPLICATIONS

This application claims benefit of priorities under 35 USC 119 to Japanese Patent Application No. 2007-146410 filed on Jun. 1, 2007, the disclosure of which are expressly incorporated by reference herein in its entirety.

FIELD OF THE INVENTION

The present invention relates to a compound having a diethylenetriamine-type metal chelate structure and a higher fatty acid triester structure linked via an ester or amide derivative. The present invention further relates to a liposome containing the compound, a chelate compound containing the compound, or a salt of either one of said compounds as a membrane component, and a contrast medium comprising the liposome.

BACKGROUND ART

A major example of non-invasive method for diagnosing arteriosclerosis includes X-ray angiography. This method contrasts vascular flows by using a water-soluble iodine-containing contrast medium, and therefore, the method has a problem of difficulty in distinguishing pathological lesions from normal tissues. By applying the above method, only a pathological lesion where constriction progresses 50% or more can be detected, and it is difficult to detect a lesion before onset of attack of an ischemic disease.

As diagnostic methods other than the above, methods of detecting a disease by nuclear magnetic resonance tomography (MRI) using a contrast medium, which is kinetically much distributed in arteriosclerotic plaques, have been reported in recent years. However, all the compounds reported as the contrast medium have a problem for use in the diagnostic methods. For example, hematoporphyrin derivatives (see, U.S. Pat. No. 4,577,636, the disclosure of which is expressly incorporated by reference herein in its entirety) are pointed out to have a defect of, for example, dermal deposition and coloring of skin. As for gadolinium complexes having a perfluorinated side chain, which have been reported to accumulate in lipid-rich plaques (see, Circulation, 109, 2890, 2004, the disclosure of which is expressly incorporated by reference herein in its entirety), accumulation in lipid-rich tissues and organs in vivo, such as fatty livers, renal epitheliums, and tendons of muscular tissues is of concern.

From a viewpoint of chemical compounds, compounds having two fatty acid ester moieties are known in which phosphatidylethanolamine (PE) and diethylenetriaminepentaacetic acid (DTPA) are bound via an amide bond (for example, Polymeric Materials Science and Engineering, 89, 148 (2003), the disclosure of which is expressly incorporated by reference herein in its entirety), and liposomes using gadolinium complexes of such compounds are also reported (Inorganica Chimica Acta, 331, 151 (2002), the disclosure of which is expressly incorporated by reference herein in its entirety). However, since these complexes are hardly soluble, they have poor property of handling in liposome formation. Accumulation and toxicity of these complexes in vivo are also of concern.

Separately reported gadolinium complexes introduced with one higher fatty acid ester group as a hydrophobic group (see, Japanese Unexamined Patent Publication (KOKAI) No. 2007-91640, the disclosure of which is expressly incorporated by reference herein in its entirety) have favorable solubility, and can also be used for liposome preparation. However, the complexes have a problem that the amount thereof to be incorporated into liposomes is limited to a low concentration. This is presumably because the complexes disclosed in the aforementioned publication are so-called wedge shape molecules, and therefore their compatibility with liposomes constituted by cylinder shape molecules is low.

DISCLOSURE OF THE INVENTION

An object of the present invention is to provide a compound suitable for a liposome contrast medium for performing lesion-selective imaging, in particular, the above compound having superior solubility and superior miscibility with membrane components of liposomes. Another object of the present invention is to provide a contrast medium such as contrast medium for MRI and contrast medium for scintigraphy comprising the above compound.

The inventors of the present invention conducted various researches to achieve the aforementioned objects. As a result, they found that a compound represented by the following general formula (I) having a diethylenetriamine-type metal chelate structure and a higher fatty acid triester structure linked via an ester or amide derivative had high water-solubility and superior properties as a component of liposomes as a contrast medium. The present invention was achieved on the basis of the aforementioned finding.

The present invention thus provides a compound represented by the following general formula (I), or a salt thereof:

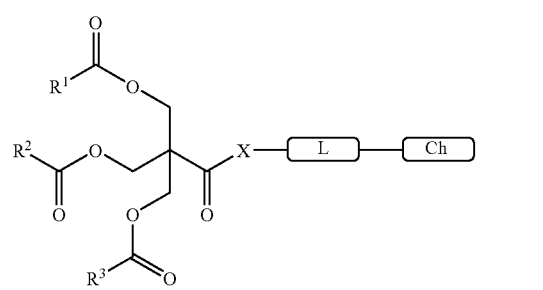

(I)

[wherein $R^1$, $R^2$ and $R^3$ independently represent an alkyl group having 8 to 25 carbon atoms, or an alkenyl group having 8 to 25 carbon atoms; X represents —O—, or —N(Z)— (Z represents hydrogen atom, or an alkyl group having 1 to 3 carbon atoms); and L represents a divalent bridging group constituted by atoms selected from the group consisting of carbon atom, hydrogen atom, oxygen atom, nitrogen atom and sulfur atom, provided that, in L, the number of oxygen atom is 0 to 8, that of nitrogen atom is 0 to 7, and that of sulfur atom is 0 to 1, and the number of carbon atom, oxygen atom, nitrogen atom and sulfur atom constituting L is 1 to 40, and number of atoms constituting main chain of L is 1 to 32; Ch represents a functional group represented by the following general formula (II):

(II)

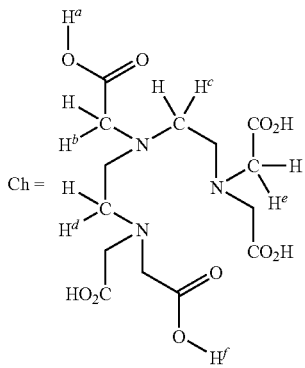

Ch = wherein any one of the hydrogen atom $H^a$, $H^b$, $H^c$, $H^d$, $H^e$, and $H^f$ is substituted with L.]

As a preferred embodiment of the aforementioned invention, there is provided the aforementioned compound or a salt thereof, wherein any one of the hydrogen atom $H^a$, $H^b$, $H^d$, and $H^f$ in Ch is substituted with L, more preferably, there is provided the aforementioned compound or a salt thereof, wherein $H^b$ or $H^d$ in Ch is substituted with L.

As another preferred embodiment of the invention, there is provided the aforementioned compound or a salt thereof, wherein $R^1$, $R^2$ and $R^3$ independently are an alkyl group having 10 to 22 carbon atoms, or an alkenyl group having 10 to 22 carbon atoms, more preferably, there is provided the aforementioned compound or a salt thereof, wherein $R^1$, $R^2$ and $R^3$ independently are an alkyl group having 10 to 22 carbon atoms.

As further preferred embodiments of the invention, there is provided the aforementioned compound or a salt thereof, wherein the number of oxygen atom is 0 to 8, that of nitrogen atom is 0 to 7, and that of sulfur atom is 0, in L, more preferably there is provided the compound or a salt thereof, wherein L represents a divalent bridging group represented by $—(CH_2)_g Y^1 COY^2 (CH_2)_h—$ (wherein $Y^1$ and $Y^2$ independently represent single bond, —O—, —NH—, or —$NCH_3$—, provided that $Y^1$ and $Y^2$ do not represent single bond at the same time, g represents an integer of 2 to 20, and h represents an integer of 1 to 4), further preferably, there is provided the compound or a salt thereof, wherein either $Y^1$ or $Y^2$ is single bond; and there is provided the aforementioned compound or a salt thereof, wherein L represents a divalent bridging group represented by $—(CH_2)_q R(CH_2CH_2Q^1)(CH_2CH_2Q^2) \ldots (CH_2CH_2Q^r)COY^3(CH_2)_s—$ (wherein $Y^3$ represents single bond, —O—, —NH—, or —$NCH_3$—, R and $Q^1$ to $Q^r$ independently represent —O—, —NH—, or —$NCH_3$—, q represents an integer of 2 to 10, r represents an integer of 1 to 5, and s represents an integer of 1 to 4, more preferably there is provided the compound or a salt thereof, wherein $Y^3$ is single bond.

The present invention also provides a chelate compound, which consists of the aforementioned compound and a metal ion, or a salt thereof. As preferred embodiments of this invention, there are provided the aforementioned chelate compound or a salt thereof, wherein the metal ion is a metal ion of an element selected from those of the atomic numbers 21 to 29, 31, 32, 37 to 39, 42 to 44, 49, and 57 to 83; and the aforementioned chelate compound or a salt thereof, wherein the metal ion is a metal ion of a paramagnetic element selected from those of the atomic numbers 21 to 29, 42, 44, and 57 to 71.

From another aspect, the present invention provides a liposome containing the aforementioned compound or a salt thereof as a membrane component, and as a preferred embodiment thereof, there is provided the liposome containing a phosphatidylcholine and a phosphatidylserine as membrane components.

From a still further aspect of the present invention, there is provided a contrast medium comprising the aforementioned liposome. As preferred embodiments of this invention, there are provided the aforementioned contrast medium, which is used for imaging of a vascular disease; the aforementioned contrast medium, which is used for imaging of vascular smooth muscle cells abnormally proliferating under influence of foam macrophages; the aforementioned contrast medium, which is used for imaging of a tissue or lesion in which macrophages localize; the aforementioned contrast medium, wherein the tissue in which macrophages localize is selected from the group consisting of tissues of liver, spleen, air vesicle, lymph node, lymph vessel, and renal epithelium; and the aforementioned contrast medium, wherein the lesion in which macrophages localize is selected from the group consisting of lesions of tumor, inflammation, and infection.

From other aspects of the present invention, there are provided use of the aforementioned compound, chelate compound, or a salt of either of said compounds for the manufacture of the aforementioned contrast medium; an imaging method comprising the step of administering liposomes containing the aforementioned compound, chelate compound, or a salt of either of said compounds as a membrane component to a mammal including human, and then performing imaging; and a method for imaging a lesion of a vascular disease, which comprises the step of administering liposomes containing the aforementioned compound, chelate compound, or a salt of either of said compounds as a membrane component to a mammal including human, and then performing imaging.

BEST MODE FOR CARRYING OUT THE INVENTION $R^1$, $R^2$, and $R^3$ independently represent an alkyl group having 8 to 25 carbon atoms, or an alkenyl group having 8 to 25 carbon atoms. The alkyl group or alkenyl group may be any of linear, branched, and cyclic groups and a group consisting of a combination thereof. The alkyl group or alkenyl group preferably has no crosslinking structure. The alkyl group or alkenyl group preferably is linear or branched groups. Although $R^1$, $R^2$, and $R^3$ may be the same or different, it is preferred that these groups are the same groups. The number of the carbon atoms constituting each of $R^1$, $R^2$, and $R^3$ is preferably 10 to 22, more preferably 13 to 19. $R^1$, $R^2$, and $R^3$ each preferably is an alkyl group. When $R^1$, $R^2$, or $R^3$ represents an alkenyl group, the double bond thereof may be in either E- or Z-configuration, or a mixture thereof, and when the alkenyl group contains two or more double bonds, the same shall apply to each double bond. Further, number and position of double bond are not particularly limited.

X represents —O— or —NZ—. Z represents hydrogen atom, or an alkyl group having 1 to 3 carbon atoms, and Z is preferably hydrogen atom or methyl group. Most preferably X is —O—.

L represents a divalent bridging group having a skeleton constituted by 1 to 40 atoms selected from the group consisting of carbon atom, oxygen atom, nitrogen atom, and sulfur atom, and suitable number of hydrogen atoms combined thereto. In L, the number of oxygen atom is 0 to 8, that of nitrogen atom is 0 to 7, and that of sulfur atom is 0 to 1, and the total number of atoms constituting the main chain (the main chain refers to an atomic group connecting X and Ch with the smallest number of atoms) of L is 1 to 32. L may be a carbon atom chain, or an atomic chain consisting of an arbitrary combination of carbon atom and hetero atom selected from the group consisting of nitrogen atom, oxygen atom, and sulfur atom. The hetero atom is preferably oxygen atom or nitrogen atom, and most preferably oxygen atom. L may also preferably consist only of carbon atom and hydrogen atom.

When the bridging group represented by L is represented by a chemical formula (general formula) in the specification, the left end shall bind to X, and the right end shall substitute any one of hydrogen $H^a$, $H^b$, $H^c$, $H^d$, $H^e$, and $H^f$ in Ch to bind to Ch. Me represents methyl group, Et represents ethyl group, $^n$Pr represents n-propyl group, and $^i$Pr represents i-propyl group.

The total number of carbon atom and hetero atom constituting L is 1 to 40, preferably 7 to 27, more preferably 10 to 25. The number of oxygen atom constituting L is 0 to 8, that of nitrogen atom is 0 to 7, and that of sulfur atom is 0 to 1, and the number of oxygen atom constituting L is preferably 2 to 7, more preferably 2 to 5. The number of nitrogen atom is preferably 0 to 4, more preferably 0 to 2. The number of sulfur atom is preferably 0.

Although L may be any of linear, branched and cyclic groups, and a group consisting of a combination thereof, a linear or branched group is preferred. The bridging group may be a saturated group, or a group containing an unsaturated bond. When L is a bridging group containing unsaturated bond, type, position and number of unsaturated bond are not particularly limited.

The total number of atoms constituting main chain of L is 1 to 32, preferably 7 to 26, more preferably 9 to 24. Main chain of L may be a carbon atom chain, or an atomic chain consisting of an arbitrary combination of carbon atom and hetero atom selected from the group consisting of oxygen atom, nitrogen atom, and sulfur atom. The hetero atom is preferably oxygen atom or nitrogen atom, and most preferably oxygen atom. Main chain of L may also preferably consist only of carbon atom. Main chain of L may be a saturated group, or a group containing an unsaturated bond, and preferably be a saturated group.

Preferred examples of L include a divalent bridging group represented by —$(CH_2)_g Y^1 COY^2 (CH_2)_h$—, wherein $Y^1$ and $Y^2$ independently represent single bond, —O—, —NH—, or —$NCH_3$—, provided that $Y^1$ and $Y^2$ do not represent single bond at the same time. Symbol g represents an integer of 2 to 20, and h represents an integer of 1 to 4. Either $Y^1$ or $Y^2$ preferably is single bond. The group wherein $Y^1$ is single bond and $Y^2$ is —O—, or $Y^1$ is —O— and $Y^2$ is single bond is most preferred. Symbol g is more preferably 4 to 20, and further preferably 4 to 16. Symbol h is most preferably 1.

Other preferred examples of L include a divalent bridging group represented by —$(CH_2)_q R(CH_2CH_2Q^1)(CH_2CH_2Q^2)\ldots(CH_2CH_2Q^r)COY^3(CH_2)_s$—. $Y^3$ represents single bond, —O—, —NH—, or —$NCH_3$—, R and $Q^1$ to $Q^r$ independently represent —O—, —NH—, or —$NCH_3$—. Symbol q represents an integer of 2 to 10, and r represents an integer of 1 to 5, and s represents an integer of 1 to 4. $Y^3$ is preferably single bond or —O—, and more preferably single bond. R and $Q^1$ to $Q^r$ are the same or different, and preferably is the same. R and $Q^1$ to $Q^r$ are most preferably —O—. Symbol q is preferably 6 to 10, r is preferably 3 to 5, and more preferably 3 to 4, and s is most preferably 1.

Ch represents a functional group represented by the following general formula (II), wherein any one of the hydrogen atom $H^a$, $H^b$, $H^c$, $H^d$, $H^e$, and $H^f$ is substituted with L.

Ch binds to L preferably with any one of the hydrogen atom $H^a$, $H^b$, $H^d$, and $H^f$ substituted with L, and most preferably with hydrogen atom $H^b$ or $H^d$ substituted with L.

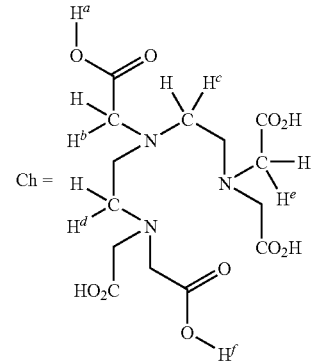

(II)

Preferred examples of the compound of the present invention will be mentioned below. However, the compound of the present invention is not limited to these examples.

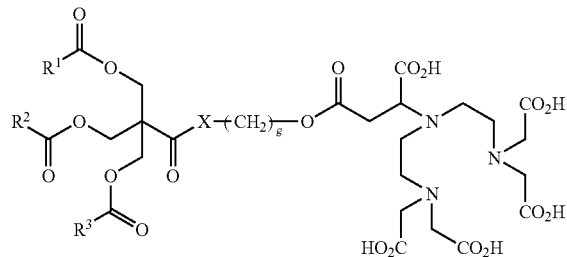

1: $R^1, R^2, R^3 = n\text{-}C_{15}H_{31}, X = O, g = 4$
2: $R^1, R^2, R^3 = n\text{-}C_{17}H_{35}, X = O, g = 5$
3: $R^1, R^2, R^3 = n\text{-}C_{15}H_{31}, X = O, g = 6$
4: $R^1, R^2, R^3 = n\text{-}C_{15}H_{31}, X = NH, g = 6$
5: $R^1, R^2, R^3 = n\text{-}C_{15}H_{31}, X = NEt, g = 6$
6: $R^1, R^2, R^3 = n\text{-}C_{15}H_{31}, X = O, g = 8$
7: $R^1, R^2, R^3 = n\text{-}C_{15}H_{31}, X = NMe, g = 8$
8: $R^1, R^2, R^3 = n\text{-}C_{15}H_{31}, X = NH, g = 10$
9: $R^1, R^2, R^3 = n\text{-}C_{19}H_{39}, X = O, g = 12$
10: $R^1, R^2, R^3 = n\text{-}C_{15}H_{31}, X = O, g = 20$

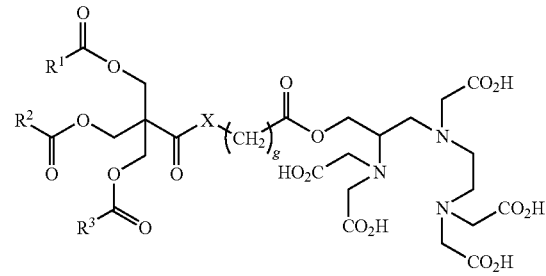

11: $R^1, R^2, R^3 = n\text{-}C_{15}H_{31}, X = O, g = 4$
12: $R^1, R^2, R^3 = n\text{-}C_{17}H_{35}, X = O, g = 7$
13: $R^1, R^2, R^3 = n\text{-}C_{13}H_{27}, X = O, g = 10$
14: $R^1, R^2, R^3 = n\text{-}C_{15}H_{31}, X = NH, g = 13$
15: $R^1, R^2, R^3 = n\text{-}C_{15}H_{31}, X = O, g = 16$
16: $R^1, R^2, R^3 = n\text{-}C_{15}H_{31}, X = NH, g = 16$
17: $R^1, R^2, R^3 = n\text{-}C_{15}H_{31}, X = O, g = 19$ -continued

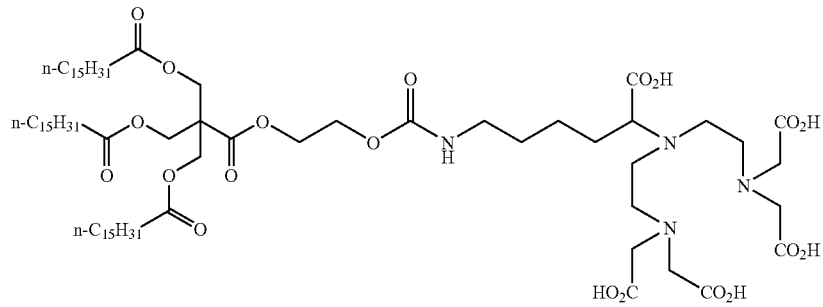

18

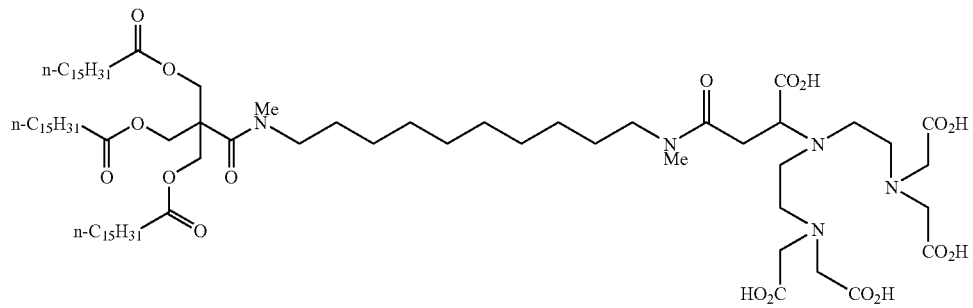

19

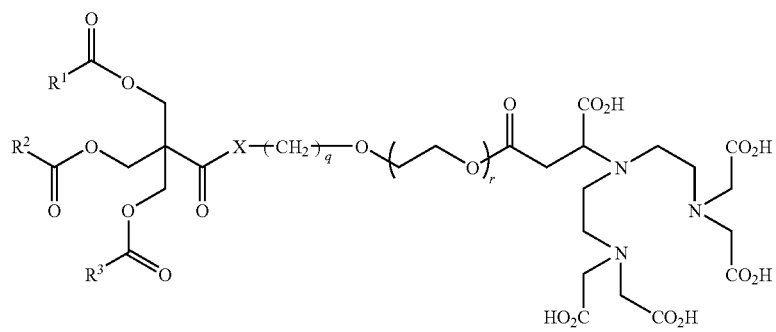

101: $R^1, R^2, R^3 = n\text{-}C_{15}H_{31}$, $X = O$, $q = 2$, $r = 3$
102: $R^1, R^2, R^3 = n\text{-}C_{15}H_{31}$, $X = O$, $g = 6$, $r = 3$
103: $R^1, R^2, R^3 = n\text{-}C_{19}H_{39}$, $X = O$, $g = 6$, $r = 4$
104: $R^1, R^2, R^3 = n\text{-}C_{15}H_{31}$, $X = NH$, $g = 6$, $r = 4$
105: $R^1, R^2, R^3 = n\text{-}C_{17}H_{35}$, $X = N^iPr$, $g = 6$, $r = 5$
106: $R^1, R^2, R^3 = n\text{-}C_{15}H_{31}$, $X = O$, $g = 8$, $r = 4$
107: $R^1, R^2, R^3 = n\text{-}C_{15}H_{31}$, $X = NMe$, $g = 8$, $r = 4$
108: $R^1, R^2, R^3 = n\text{-}C_{13}H_{27}$, $X = O$, $g = 10$, $r = 2$
109: $R^1, R^2, R^3 = n\text{-}C_{15}H_{31}$, $X = NH$, $g = 10$, $r = 3$
110: $R^1, R^2, R^3 = n\text{-}C_{15}H_{31}$, $X = O$, $g = 10$, $r = 4$ -continued
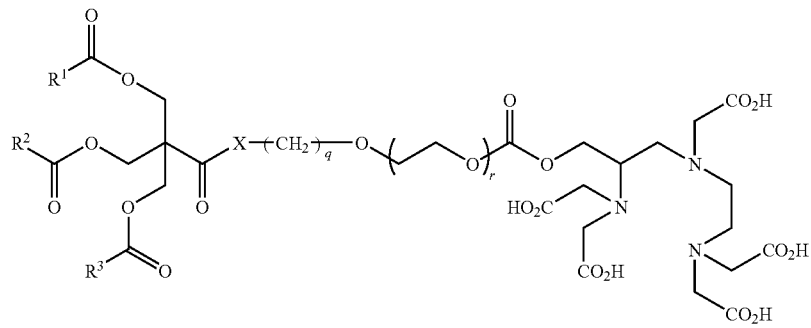
111: R¹, R², R³ = n-C₁₅H₃₁, X = O, q = 4, r = 3
112: R¹, R², R³ = n-C₁₅H₃₁, X = NH, g = 4, r = 3
113: R¹, R², R³ = n-C₁₅H₃₁, X = O, g = 7, r = 4
114: R¹, R², R³ = n-C₁₅H₃₁, X = O, g = 10, r = 2
115: R¹, R², R³ = n-C₁₇H₃₅, X = O, g = 10, r = 4
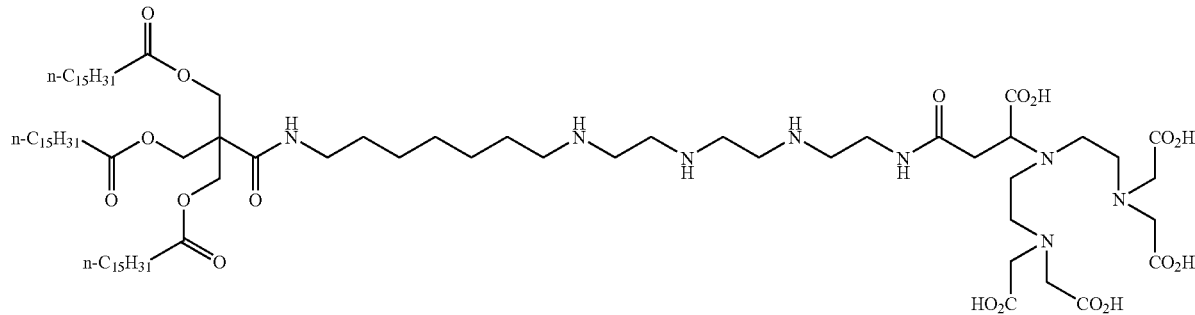
116
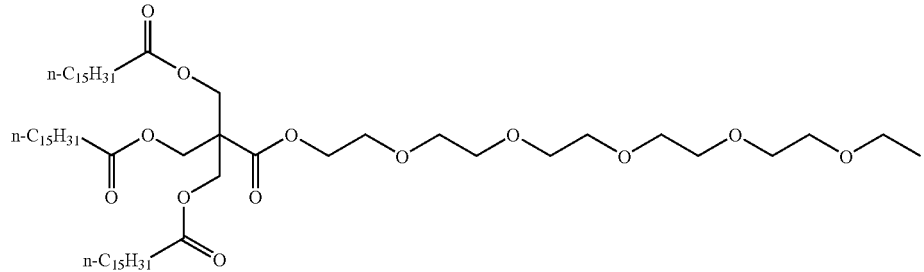
117
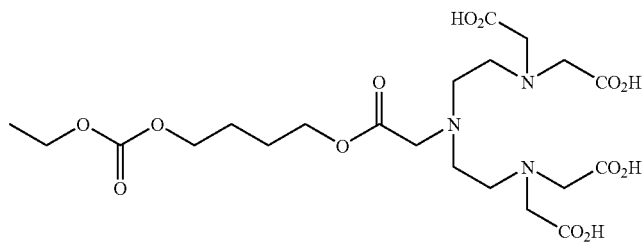

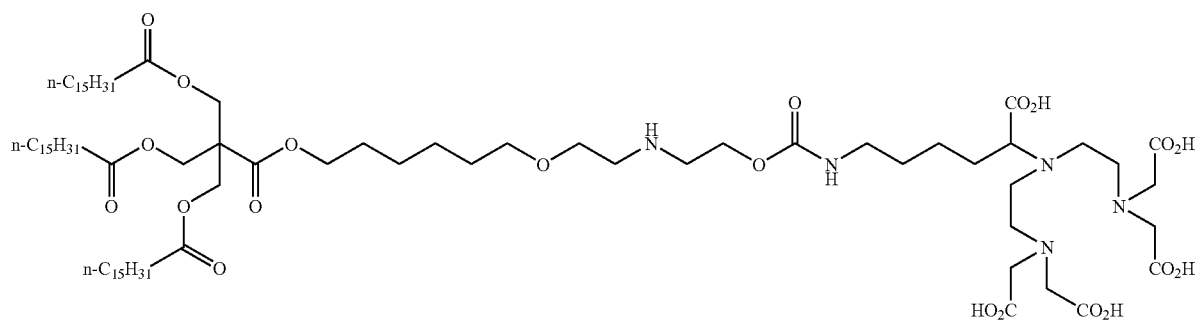
118
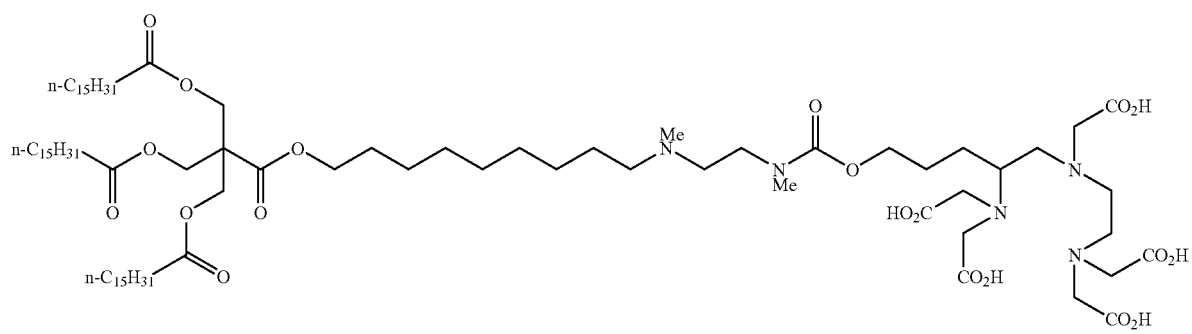
119
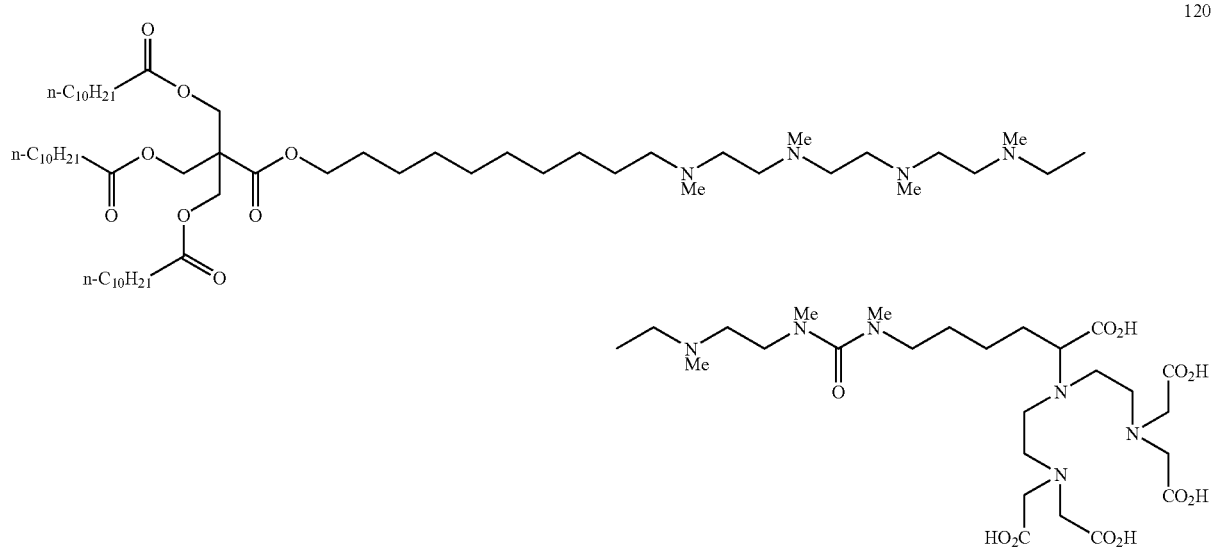
120
201
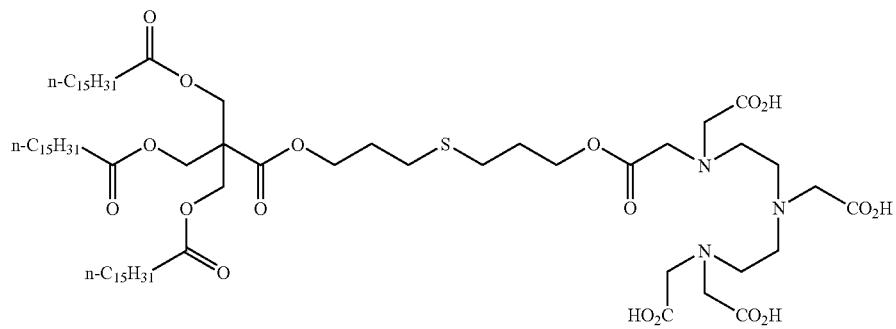

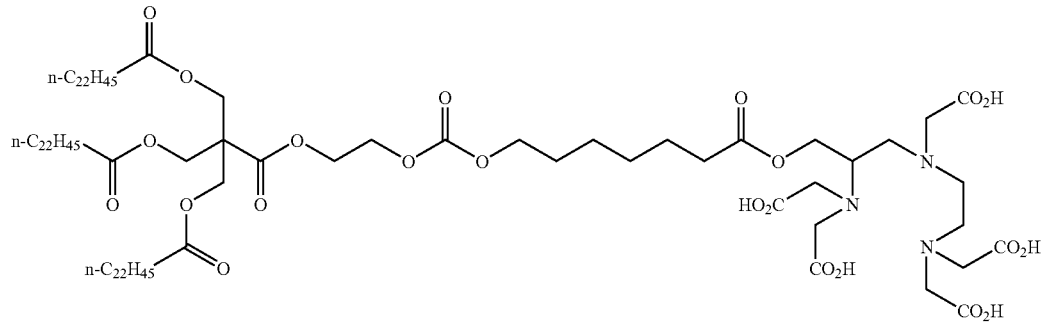
202
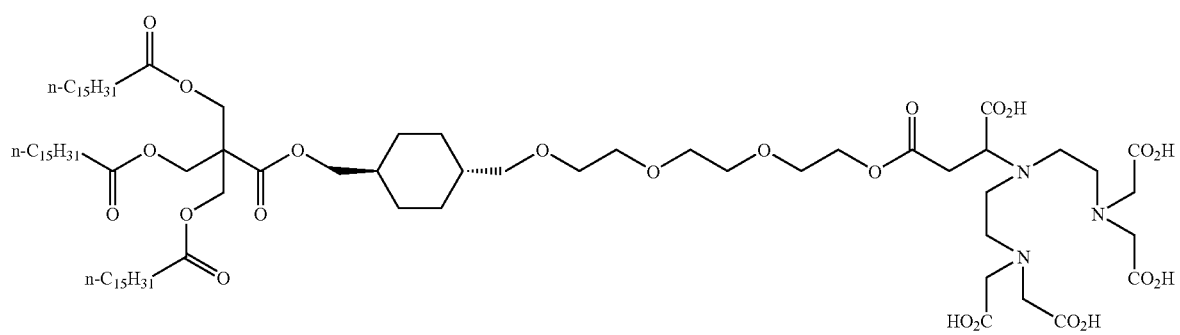
203
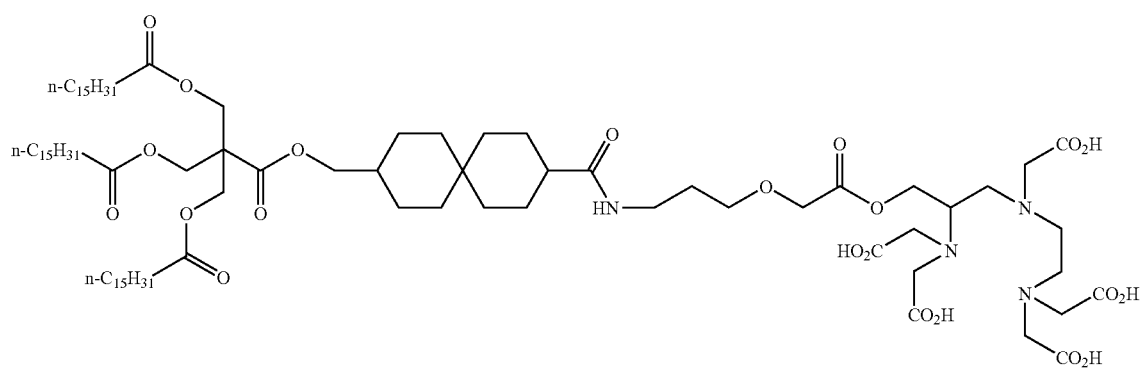
204
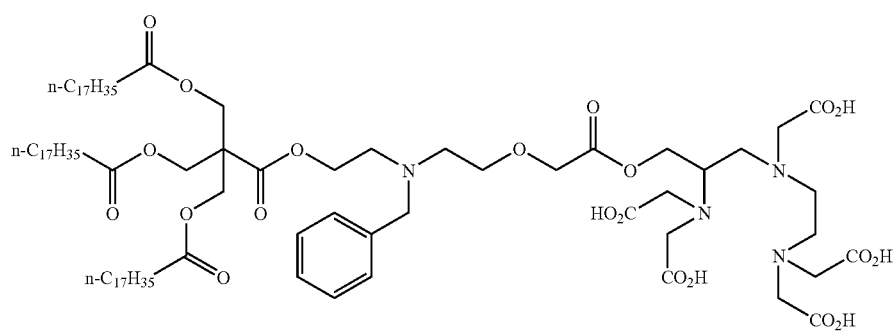
205

-continued
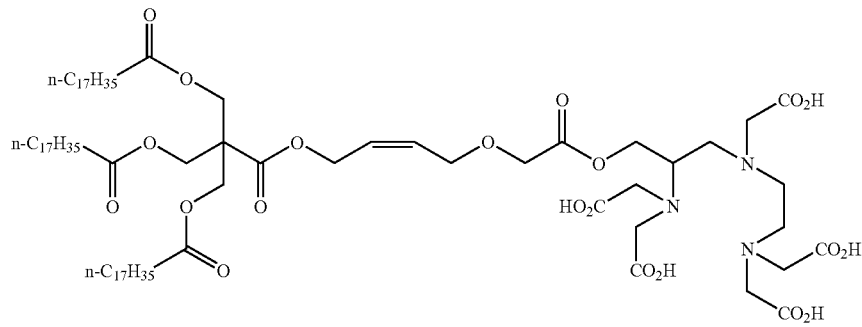
206
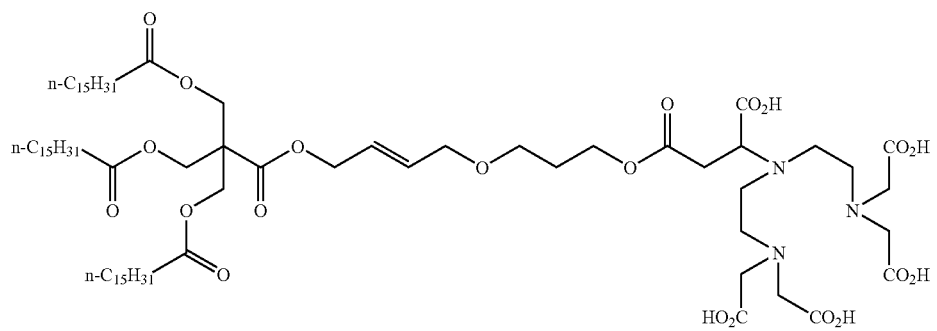
207
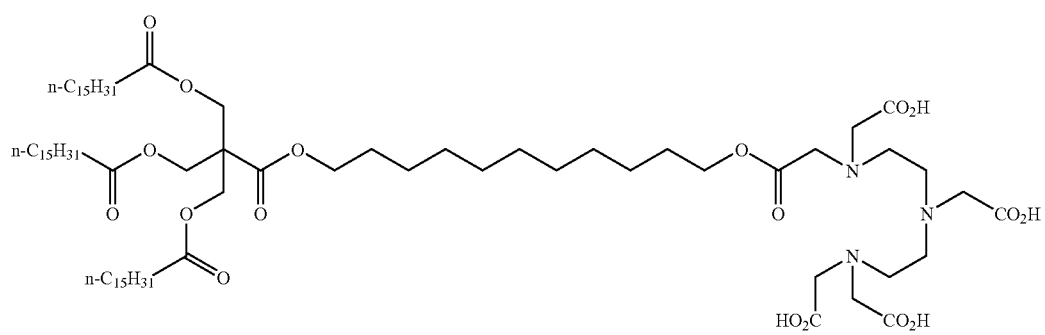
301
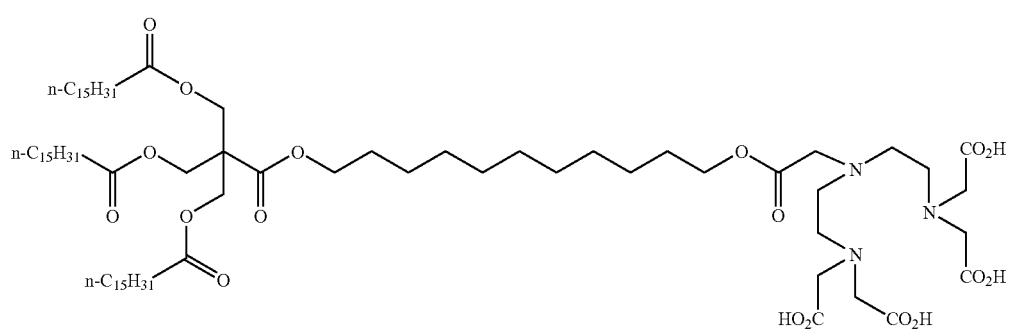
302

-continued
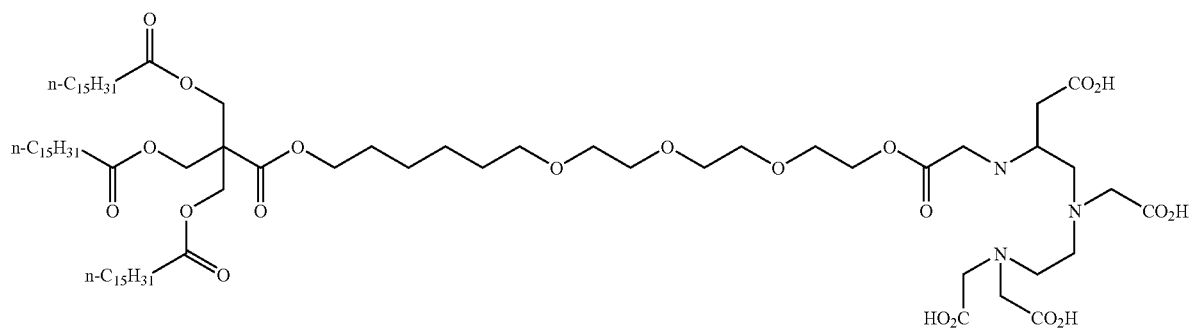
303
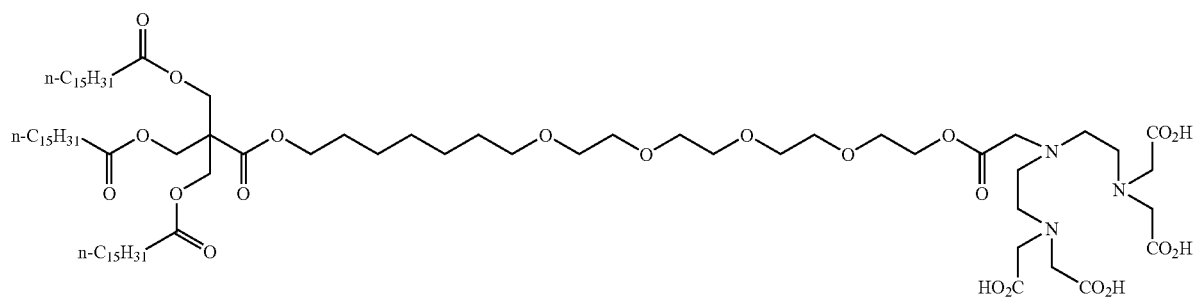
304
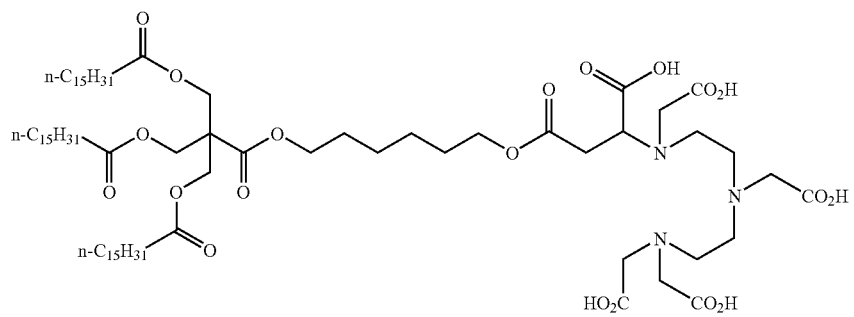
305
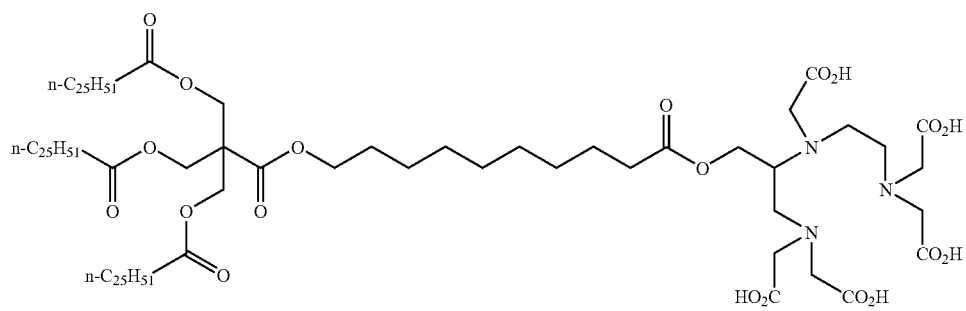
306
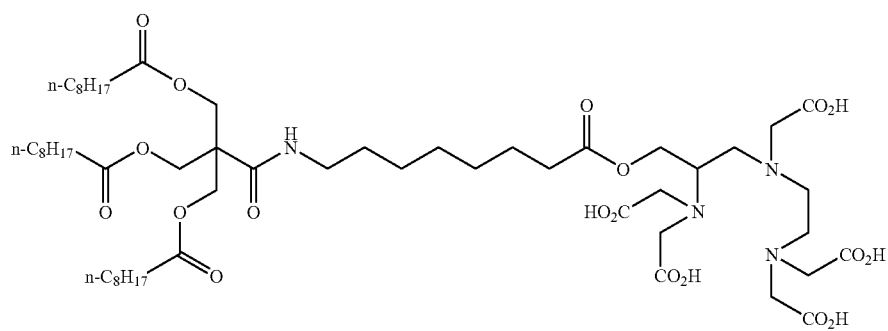
307

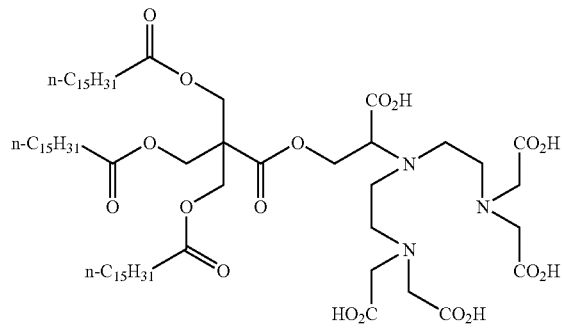
308
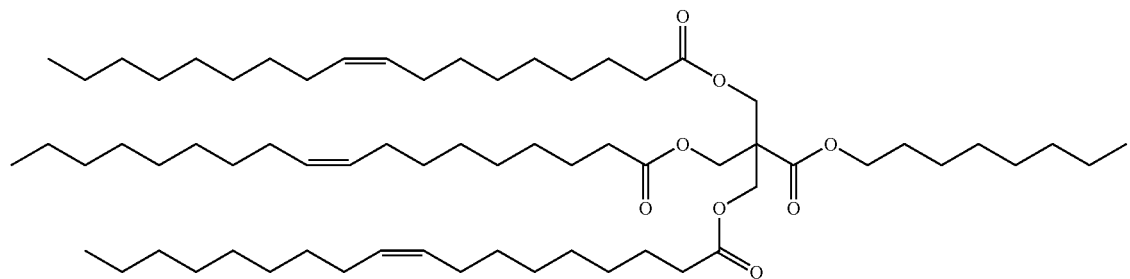
401
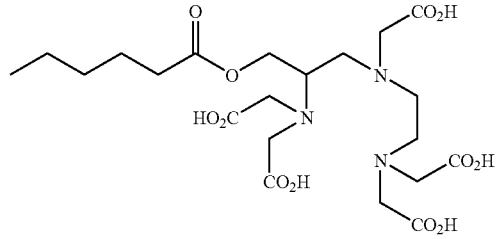
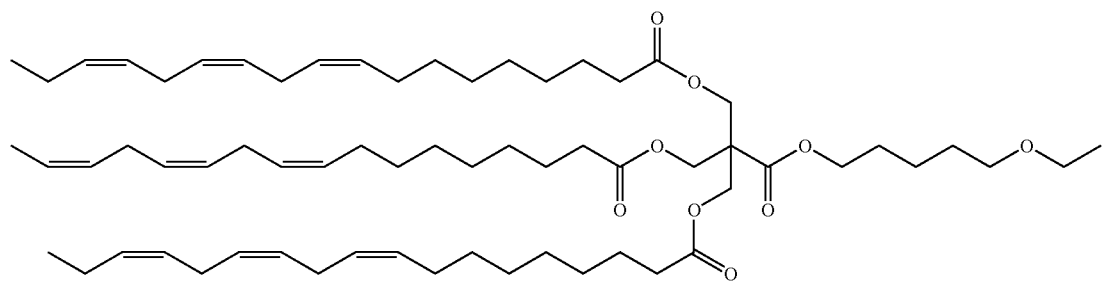
402
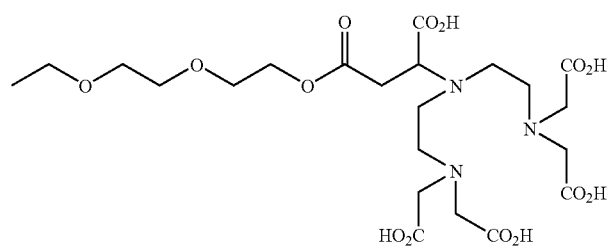

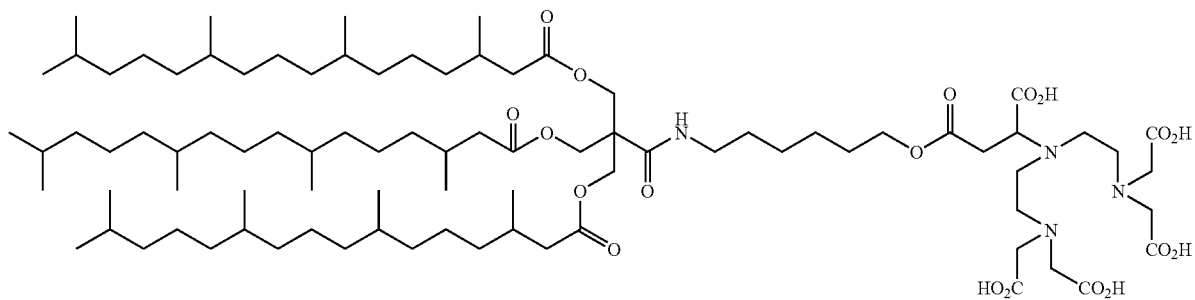

403

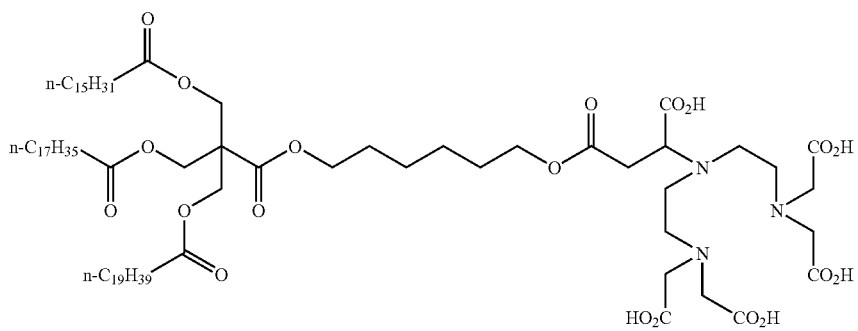

404

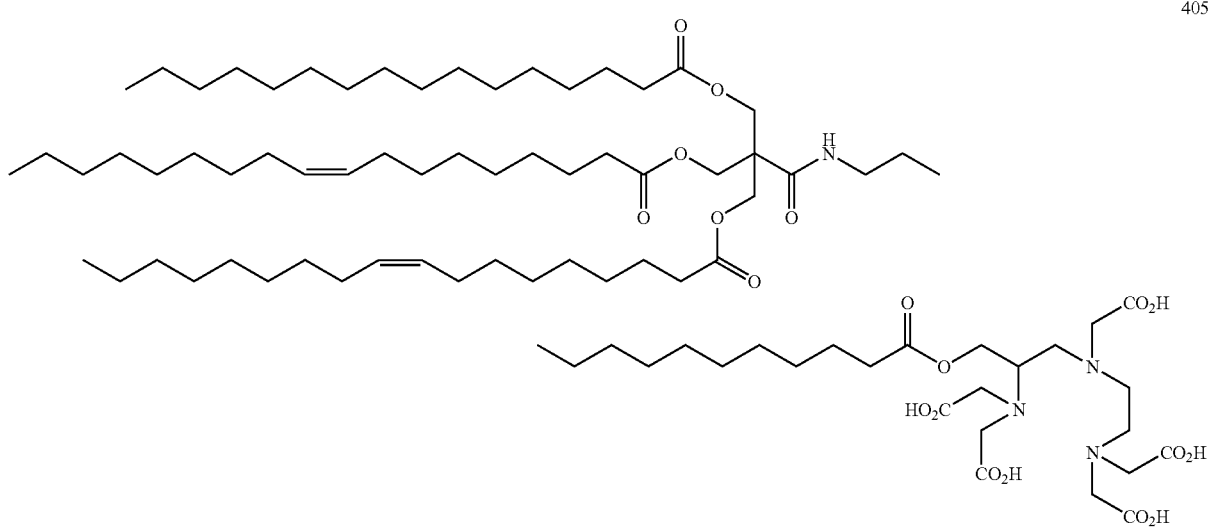

405

Synthetic methods for the compound of the present invention, in general, will be explained. However, synthetic methods of the compound of the present invention are not limited to these methods. As the long chain fatty acids as a partial structure of the compound of the present invention, those ordinarily commercially available may be used, or they may be suitably synthesized depending on purposes. When they are obtained by syntheses, corresponding alcohols, alkyl halides and the like can be used as raw materials according to, for example, the method described by Richard C. Larock in Comprehensive Organic Transformations (VCH), the disclosure of which is expressly incorporated by reference herein in its entirety.

The aforementioned long chain fatty acids can be condensed with a pentaerythritol derivative to form a triacyl compound, then the remained hydroxy group is oxidized to form a carboxylic acid. The carboxylic acid can be coupled with an α,ω-diol or diamine, such as diethylene glycol, diethanolamine, and diethylenetriamine, an α-amino-ω-alcohol, ω-haloalcohol, or the like, and thereby derived into a triacyl-ω-alcohol, amine, or halide (which may be chloride, bromide, or iodide). In this process, a protective group can also be used, if necessary. As a protective group used in such process, for example, any of the protective groups described by T. W. Green & P. G. M. Wuts in Protecting Groups in Organic Synthesis (John Wiley & Sonc, Inc.), the disclosure of which is expressly incorporated by reference herein in its entirety, can be suitably selected and used.

The aforementioned triacyl-ω-alcohol, amine, or halide compound can be bound with a polyamine derivative having a metal coordinating ability to synthesize the compound of the present invention. As for the method for preparation, the compound can be synthesized according to, for example, the method described in Bioconjugate Chem., 10, 137 (1999), the disclosure of which is expressly incorporated by reference herein in its entirety. However, this method is a mere example, and the method is not limited to the above method.

The chelate compound of the present invention consists of the aforementioned compound and a metal ion. Although type of the metal ion is not particularly limited, metal ions of paramagnetic metals, heavy metals, and radioactive metals of radioactive metal isotopes are preferably used as metal ions suitable for the purpose of imaging by MRI, X-ray, ultrasonic contrast, positron emission tomography (PET), scintigraphy, and the like, or radiotherapy. More specifically, metal ions of elements selected from those of the atomic numbers 21 to 29, 31, 32, 37 to 39, 42 to 44, 49, and 57 to 83 are preferred. Examples of metal ions suitable for use of the chelate compound of the present invention as a contrast medium for MRI include metal ions of elements of the atomic numbers 21 to 29, 42, 44 and 57 to 71. For use in the preparation of positive MRI contrast medium, more preferred metals are those of the atomic numbers 24 (Cr), 25 (Mn), 26 (Fe), 63 (Eu), 64 (Gd), 66 (Dy), and 67 (Ho). For use in the preparation of negative MRI contrast medium, more preferred metals are those of the atomic numbers 62 (Sm), 65 (Tb), and 66 (Dy). Most preferred are those of the atomic numbers 25 (Mn), 26 (Fe), and 64 (Gd), and Mn(II), Fe(III), and Gd(III) are especially preferred.

The compound or chelate compound of the present invention which has a radioactive isotope can be used as a contrast medium for scintigraphy. As the radioactive isotope used for the purpose of being incorporated in the compound, examples include, but not limited to $^{67}$Ga, $^{81m}$Kr, $^{99m}$Tc, $^{111}$In, $^{123}$I, $^{131}$I, $^{133}$Xe, and $^{201}$Tl.

The compound or chelate compound of the present invention having one or more nuclear species emitting positrons may be used for imaging by PET. More specifically, besides the aforementioned chelate compound, a compound obtained by incorporating a nuclear species emitting positrons into the compound of the present invention can be preferably used as a medium for the imaging. Preferred examples of the nuclear species used for the purpose of the incorporation into the compound include $^{11}$C, $^{13}$N, $^{15}$O, and $^{18}$F. More preferred nuclear species are $^{11}$C and $^{18}$F.

The compound and chelate compound of the present invention may have one or more asymmetric centers. In such compounds, stereoisomers such as optically active substances and diastereomers based on the asymmetric centers may exist. Any of arbitrary stereoisomers in pure forms, arbitrary mixtures of stereoisomers, racemates and the like fall within the scope of the present invention. Further, the compound of the present invention may have one or more olefinic double bonds. The configuration thereof may be either E-configuration or Z-configuration, or the compound may be present as a mixture thereof. The compound of the present invention may also exist as tautomers. Any tautomers or mixtures thereof fall within the scope of the present invention. Further, the compound of the present invention may form a salt, and the compound in a free form and the compound in the form of a salt may form a hydrate or a solvate. All of these substances also fall within the scope of the present invention. Type of the salt is not particularly limited, and the salt may be an acid addition salt, or a base addition salt.

The compound or the chelate compound of the present invention or a salt thereof can be used as a membrane component of a liposome. When a liposome is prepared by using the compound or the chelate compound of the present invention or a salt thereof, amount of the compound or the chelate compound of the present invention or a salt thereof is about from 10 to 90 mass %, preferably from 10 to 80 mass %, more preferably from 20 to 80 mass %, based on the total mass of membrane components. Although one kind of the compound of the present invention may be used as the membrane component, two or more kinds of the compounds may be used in combination.

As other membrane components of liposome, any of lipid compounds ordinarily used for the preparation of liposomes can be used. Such compounds are described in, for example, Biochim. Biophys. Acta, 150 (4), 44 (1982); Adv. in Lipid. Res., 16 (1) 1 (1978); RESEARCH IN LIPOSOMES, P. Machy, L. Leserman, John Libbey EUROTEXT Co.; "Liposome", Ed., Nojima, Sunamoto and Inoue, Nankodo, and the like, the disclosures of which are each expressly incorporated by reference herein in their entireties. As the lipid compounds, phospholipids are preferred, and phosphatidylcholines (PC) are particularly preferred. Preferred examples of phosphatidylcholines include egg PC (PC derived from egg), dimyristoyl-PC (DMPC), dipalmitoyl-PC (DPPC), distearoyl-PC (DSPC), dioleyl-PC (DOPC), and the like. However, PCs are not limited to these examples.

Preferred examples of the membrane components of liposomes include a combination of a phosphatidylcholine and a phosphatidylserine (PS). Examples of the phosphatidylserine include those having lipid moieties similar to those of the phospholipids mentioned as preferred examples of the phosphatidylcholines. When a phosphatidylcholine and a phosphatidylserine are used in combination, molar ratio of PC and PS (PC:PS) used is preferably in the range of 90:10 to 10:90, more preferably 30:70 to 70:30.

Another preferred embodiment of the liposome of the present invention includes a liposome containing a phosphatidylcholine and a phosphatidylserine and further containing a phosphoric acid dialkyl ester as membrane components. The two alkyl groups constituting the dialkyl ester of phosphoric acid dialkyl ester are preferably the same, and each alkyl group preferably contains 6 or more carbon atoms, more preferably 10 or more carbon atoms, still more preferably 12 or more carbon atoms. Preferred examples of the phosphoric acid dialkyl ester include, but not limited to, dilauryl phosphate, dimyristyl phosphate, dicetyl phosphate and the like. In this embodiment, preferred amount of the phosphoric acid dialkyl ester is from 1 to 50 mass %, more preferably from 1 to 30 mass %, still more preferably from 1 to 20 mass %, based on the total mass of phosphatidylcholine and phosphatidylserine.

In the liposome containing a phosphatidylcholine, a phosphatidylserine, a phosphoric acid dialkyl ester and the compound or chelate compound of the present invention as membrane components, preferred mass ratios of PC, PS, phosphoric acid dialkyl ester and the compound (and the chelate compound) of the present invention is from 5 to 40 mass %: from 5 to 40 mass %: from 1 to 10 mass %: from 15 to 80 mass %.

The components of the liposome of the present invention are not limited to the aforementioned four kinds of compounds, and other components may be admixed. Examples of such components include cholesterol, cholesterol esters, sphingomyelin, monosial ganglioside GM1 derivatives described in FEBS Lett., 223, 42 (1987); Proc. Natl. Acad. Sci., USA, 85, 6949 (1988) and the like, the disclosures of which are each expressly incorporated by reference herein in their entireties, glucuronic acid derivatives described in Chem. Lett., 2145 (1989); Biochim. Biophys. Acta, 1148, 77 (1992) and the like, the disclosures of which are each expressly incorporated by reference herein in their entireties, and polyethylene glycol derivatives described in Biochim. Biophys. Acta, 1029, 91 (1990); FEBS Lett., 268, 235 (1990)

and the like, the disclosures of which are each expressly incorporated by reference herein in their entireties. However, the components are not limited to these examples.

The liposome of the present invention may be prepared by any methods available for those skilled in this field. Examples of the preparation methods are described in Ann. Rev. Biophys. Bioeng., 9, 467 (1980), "Liopsomes" (Ed. by M. J. Ostro, MARCELL DEKKER, INC.) and the like, the disclosures of which are each expressly incorporated by reference herein in their entireties, as well as the published reviews of liposomes mentioned above. More specifically, examples include the ultrasonication method, ethanol injection method, French press method, ether injection method, cholic acid method, calcium fusion method, freeze and thawing method, reverse phase evaporation method and the like. However, the preparation methods are not limited to these examples. Size of the liposome of the present invention may be any of those obtainable by the aforementioned methods. Generally, the size in average may be 400 nm or less, preferably 200 nm or less. Structure of the liposome is not also particularly limited, and may be any structure such as unilamellar or multilamellar structure. It is also possible to formulate one or more kinds of appropriate medicaments or other contrast media in the liposome.

When the liposomes of the present invention are used as a contrast medium, it can be preferably administered parenterally, more preferably intravenously administered. For example, preparations in the form of an injection or a drip infusion can be provided as powdery compositions in a lyophilized form, and they can be used by being dissolved or resuspended just before use in water or an appropriate solvent (e.g., physiological saline, glucose infusion, buffering solution and the like). When the liposomes of the present invention are used as a contrast medium, the dose can be suitably determined so that the content of compounds in the liposomes becomes similar to that of a conventional contrast medium.

Although it is not intended to be bound by any specific theory, it is known that, in vascular diseases such as arteriosclerosis or restenosis after percutaneous transluminal coronary angioplasty (PTCA), vascular smooth muscle cells constituting tunica media of blood vessel abnormally proliferate and migrate into endosporium at the same time to narrow blood flow passages. Although triggers that initiate the abnormal proliferation of normal vascular smooth muscle cells have not yet been clearly elucidated, it is known that migration into endosporium and foaming of macrophages are important factors. It is reported that vascular smooth muscle cells then cause phenotype conversion (from constricted to composite type).

If the liposomes of the present invention are used, the compound serving as a defined contrast medium can be selectively taken up into the vascular smooth muscle cells abnormally proliferating under influences of foam macrophages. As a result, imaging becomes possible with high contrast between vascular smooth muscle cells of a lesion and a non-pathological site. Therefore, the contrast medium of the present invention can be suitably used particularly for MRI of vascular diseases. For example, imaging of arteriosclerotic lesion or restenosis after PTCA can be performed.

Further, as described in, for example, J. Biol. Chem., 265, 5226 (1990), the disclosure of which is expressly incorporated by reference herein in its entirety, it is known that liposomes containing phospholipids, in particular, liposomes formed from PC and PS, are likely to accumulate on macrophages with the aid of scavenger receptors. Therefore, by using the liposomes of the present invention, the compound of the present invention can be accumulated in a tissue or a lesion in which macrophages localize. If the liposomes of the present invention are used, a predetermined compound can be accumulated in macrophages in a larger amount compared with the case of using suspension or oil emulsion belonging to known techniques.

Examples of tissues in which localization of macrophages is observed, which can be suitably imaged by the method of the present invention, include blood vessel, liver, spleen, air vesicle, lymph node, lymph vessel, and renal epithelium. Further, it is known that macrophages accumulate in lesions in certain classes of diseases. Examples of such diseases include tumor, arteriosclerosis, inflammation, infection and the like. Therefore, lesions of such diseases can be identified by using the liposomes of the present invention. In particular, it is known that foam macrophages, which take up a large amount of denatured LDL with the aid of scavenger receptors, accumulate in atherosclerosis lesions at an early stage (Am. J. Pathol., 103, 181 (1981); Annu. Rev. Biochem., 52, 223 (1983), the disclosures of which are each expressly incorporated by reference herein in their entireties). Therefore, by performing imaging after accumulation of the liposomes of the present invention in the macrophages, it is possible to identify locations of atherosclerosis lesions at an early stage, which is hardly achievable by other means.

The imaging method using the liposomes of the present invention is not particularly limited. For example, imaging can be attained by measuring change in the T1/T2 relaxation time of water in the same manner as that in imaging methods using a usual contrast medium for MRI. Moreover, it is also possible to use the liposomes as a contrast medium for scintigraphy, X-ray contrast medium, optical image formation agent, and ultrasonic contrast agent by suitably using an appropriate metal ion.

EXAMPLES

The present invention will be explained more specifically with reference to the following examples. However, the scope of the present invention is not limited to the following examples. The compound number in the examples corresponds to that in the above-listed compounds.

Example 1

Compound 3, in which $R^1$, $R^2$ and $R^3$ are the same, X is —O—, and hydrogen atom Hb in Ch is substituted with L, was prepared according to the following scheme. "A" prepared according to the method described in Euro. J. Org. Chem., 19, 3979 (2004), the disclosure of which is expressly incorporated by reference herein in its entirety, is oxidized by using chromic acid to obtain carboxylic acid B. "B" and boromohexanol were condensed by using a condensing agent, EDC (1-ethyl-3-(3-dimethylamino)propylcarbodiimide hydrochloride), to obtain Compound C. Compound C is linked with a separately-prepared chelating ligand moiety D by using potassium carbonate to obtain Compound E. Deprotection of the t-butyl ester was performed under an acidic condition to synthesize Compound 3, and by allowing gadolinium chloride to act on Compound 3, Complex 3-Gd was successfully obtained.

Compound E: $^1$H-NMR(300 MHz, $CDCl_3$) δ: 4.28(6H, s), 4.13(2H, t), 4.03(2H, t), 3.77(1H, dd), 3.42(8H, s), 2.76(1H, dd), 2.72-2.76(8H, m), 2.48(1H, dd), 2.28(6H, t), 1.50-1.66 (10H, m), 1.48(45H, s), 1.20-1.47(76H, m), 0.87(9H, t)

Compound 3: Mass (ESI): m/z 1398.6 $(M+H)^+$

Compound 3-Gd: Mass (ESI): m/z 775.3 $(M-2Na)^{2-}/2$

In the following scheme, t-Bu represents tertiary butyl group, Me represents methyl group, and DMAc represents dimethylacetamide.

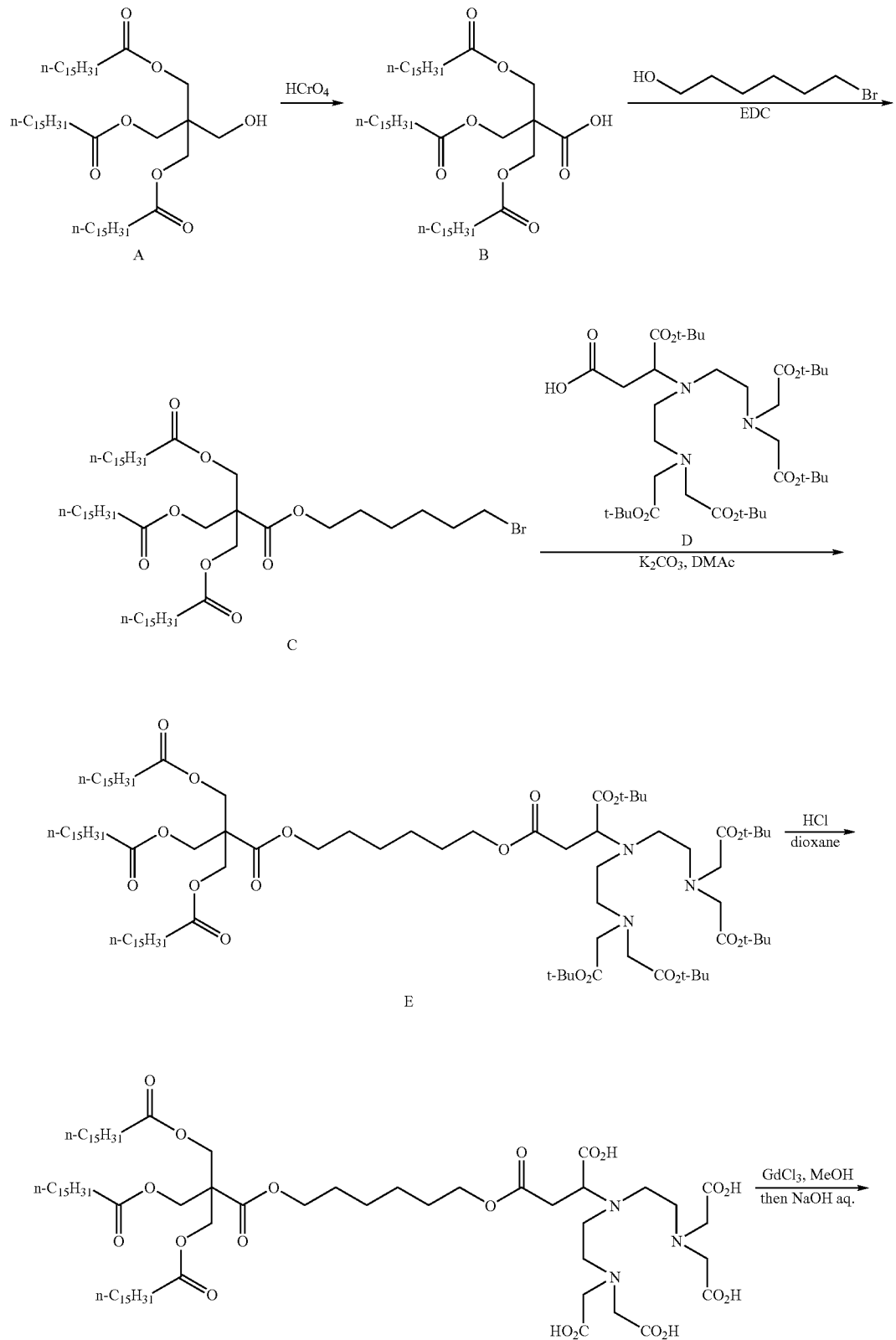

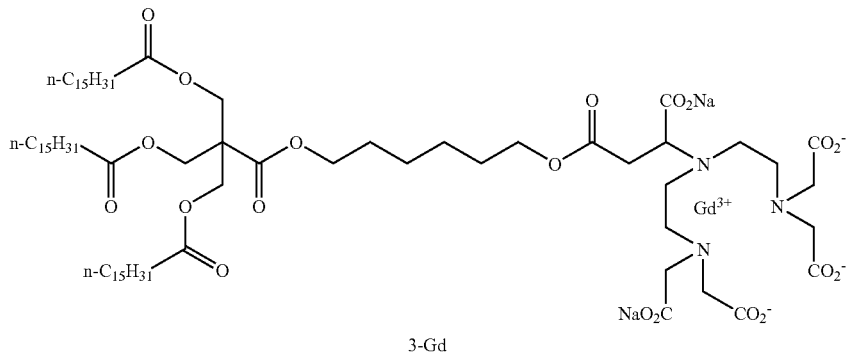

3-Gd

Example 2

Compound 4, in which X is —NH— was prepared according to the following scheme. The carboxylic acid B and aminohexanol were condensed by using a condensing agent, EDC, to obtain Compound F. Compound F is linked with a separately prepared chelating ligand moiety D by using triphenylphosphine, DMAD (dimethyl azodicarboxylate) to obtain Compound G. Deprotection of the t-butyl ester was performed under an acidic condition to synthesize Compound 4, and by allowing gadolinium chloride to act on Compound 4, Complex 4-Gd was successfully obtained.

Compound G: $^1$H-NMR(300 MHz, CDCl$_3$)δ: 6.14(1H, d), 4.31(6H, s), 4.03(2H, t), 3.76(1H, dd), 3.42(8H, s), 3.26(2H, dt), 2.76(1H, dd), 2.72-2.76(8H, m), 2.48(1H, dd), 2.28(6H, t), 1.50-1.66(10H, m), 1.48(45H, s), 1.20-1.47(76H, m), 0.87 (9H, t)

Compound 4: Mass (ESI): m/z 1397.7 (M+H)$^+$

Complex 4-Gd: Mass (ESI): m/z 774.6 (M−2Na)$^{2-}$/2

In the following scheme, Ph represents phenyl group, t-Bu represents tertiary butyl group, and Me represents methyl group, and THF represents tetrahydrofuran.

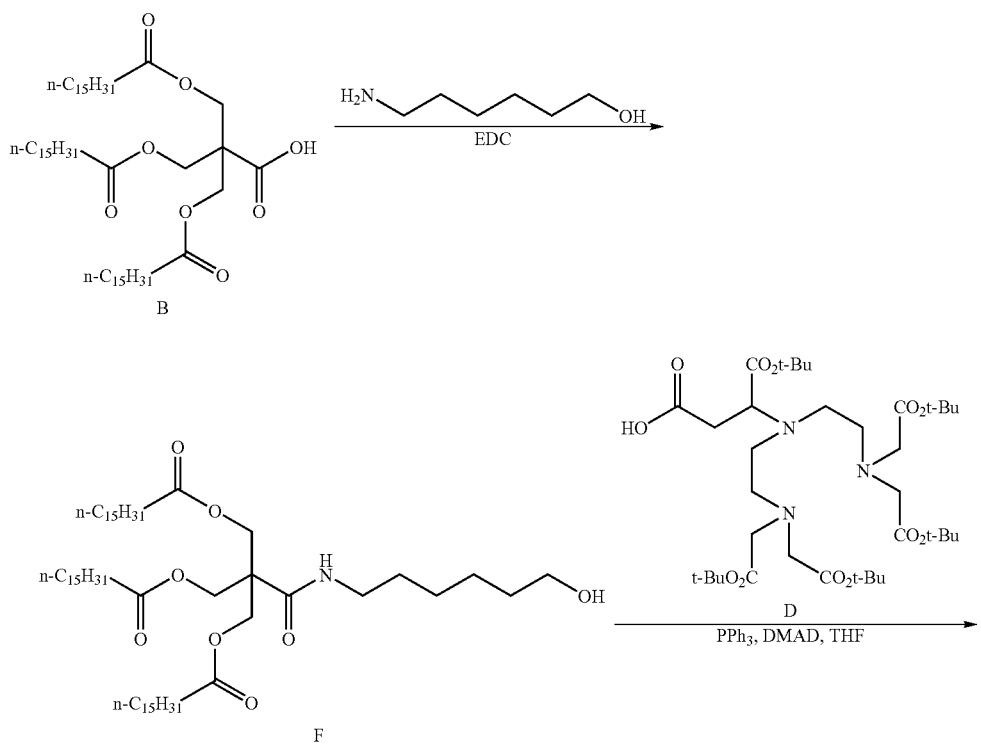

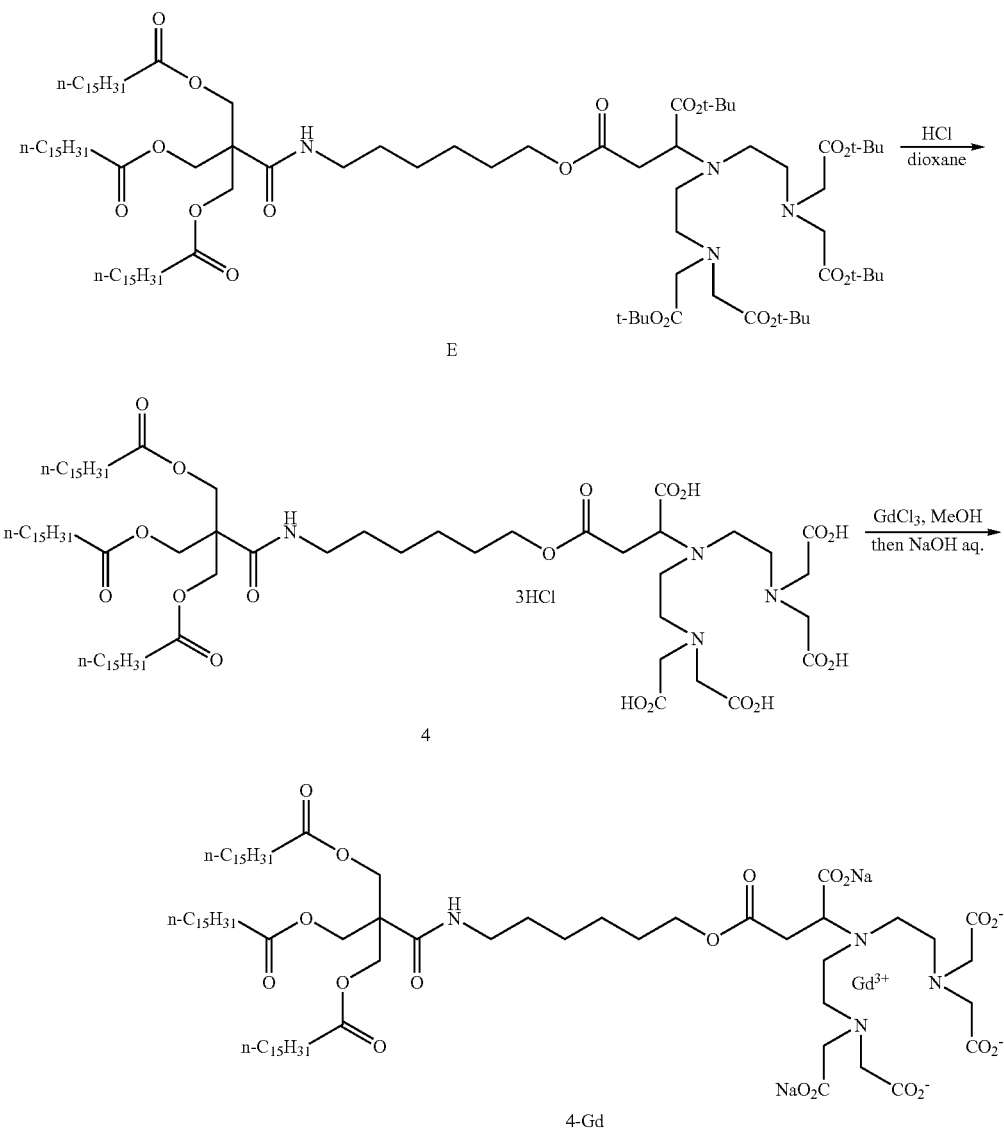

Test Example 1

Solubility Test

The above-prepared Compound 3-Gd and Compound 4-Gd was weighed in an amount giving a concentration of 1 mM, and added with 1 ml of a mixed solvent of chloroform/methanol (1/1), and solubility in the solvent was examined (at room temperature of 25° C.). As a result, the compounds of the present invention formed uniform solutions, and thus it is clearly understood that they have superior features for preparation of liposomes. Similarly, the above-prepared Compound 3-Gd and Compound 4-Gd was weighed in an amount giving a concentration of 1 mM, and added with 1 ml of chloroform, and solubility in the solvent was examined (at room temperature of 25° C.). As a result, the compounds of the present invention formed uniform solutions.

Test Example 2

Preparation of Liposomes

According to the method described in J. Med. Chem., 25 (12), 1500 (1982), dipalmitoyl-PC (Funakoshi, No. 1201-41-0225), dipalmitoyl-PS (Funakoshi, No. 1201-42-0237), and each of the gadolinium complexes were dissolved in chloroform contained in an eggplant-shaped flask to form a uniform solution, and then the solvent was evaporated under reduced pressure to form a thin membrane on the bottom of the flask. The thin membrane was dried in vacuo, then added with an appropriate volume of 0.9% physiological saline (Hikari Pharmaceutical, No. 512) and ultrasonicated (probe type oscillator, Branson, No. 3542, 0.1 mW) for 5 minute with ice cooling, and then a liposome preparation apparatus (Central Kagaku) was used to obtain a uniform liposome dispersion in which particles had sizes of 85 to 120 nm.

After dipalmitoyl PC: dipalmitoyl PS: Compound 3-Gd at concentration ratio of 50 nmol: 50 nmol: 10 nmol was solvated in 1 ml of chloroform, the above method was conducted, and liposome dispersion was successfully obtained.

Test Example 3

Toxicity test by Continuous Administration for 3 Days in Mice

Six-week old ICR male mice (Charles River Japan) were purchased, and after quarantine for 1 week, acclimatized for 1 week in a clean animal cage (air-conditioning: HEPA filter of class 1000, room temperature: 20 to 24° C., humidity: 35 to 60%). Then, in order to obtain the MTD (maximum tolerated dose) value, a mouse serum suspension of a test compound was given from the caudal vein. The mouse serum suspension of a test compound was given by using physiological saline (Hikari Pharmaceutical) or a glucose solution (Otsuka Pharmaceutical) as a solvent. Then, on the basis of the MTD value obtained, Gd complex was given everyday from the caudal vein for three consecutive days in an amount corresponding to ½ of the MTD value (n=3). The symptoms were observed up to 6 hours after each administration to observe neurotoxicity, and then autopsy was performed to examine major organs.

As the results that the above Test was conducted by using Compound 3-Gd as the test compound, MTD value was 400 mg/kg, showing the low-toxicity of the compound. Compound 3-Gd was given everyday from the caudal vein for three consecutive days in an amount corresponding to ½ of the MTD value (n=3). As the result, no neurotoxicity was observed.

It was successfully confirmed that the compounds of the present invention had low toxicity and no neurotoxicity. Thus, it is clearly understood that the compounds of the present invention have superior characteristics as a component lipid of liposomes for contrast medium.

Further, Gadolinium MRI contrast imaging can be conducted by targeting a lesion in arch of twelve-month old WHHL rabbit (Kitayama Labes) having lesion formed in aotic arch, which has been kept for acclimatization for 1 week after being available, and received administration of the liposome formulation obtained as above from subaural vein.

INDUSTRIAL APPLICABILITY

The compound, chelate compound, and a salt of either of said compounds according to the present invention have superior properties as a component lipid of liposomes for contrast medium, and a lesion of a vessel can be selectively contrasted by performing imaging using liposomes containing the compound.

The invention claimed is:

1. A compound represented by the following general formula (I), or a salt thereof:

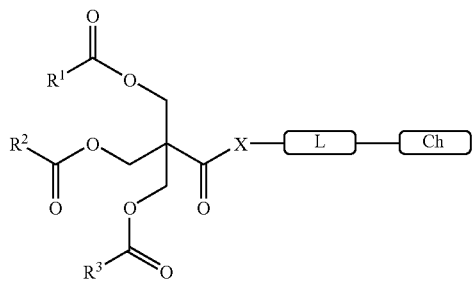

(I)

wherein $R^1$, $R^2$ and $R^3$ independently represent an alkyl group having 8 to 25 carbon atoms, or an alkenyl group having 8 to 25 carbon atoms; X represents —O—, or —N(Z)— (Z represents hydrogen atom, or an alkyl group having 1 to 3 carbon atoms); and L represents a divalent bridging group constituted by atoms selected from the group consisting of carbon atom, hydrogen atom, oxygen atom, nitrogen atom and sulfur atom, provided that, in L, the number of oxygen atom is 0 to 8, that of nitrogen atom is 0 to 7, and that of sulfur atom is 0 to 1, and the number of carbon atom, oxygen atom, nitrogen atom and sulfur atom constituting L is 1 to 40, and number of atoms constituting main chain of L is 1 to 32; Ch represents a functional group represented by the following general formula (II):

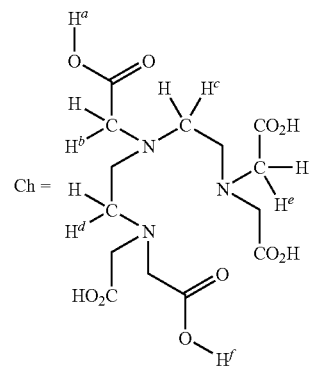

(II)

wherein any one of the hydrogen atom $H^a$, $H^b$, $H^c$, $H^d$, $H^e$, and $H^f$ is substituted with L.

2. The compound or a salt thereof according to claim 1, wherein $H^b$ or $H^d$ in Ch is substituted with L.

3. The compound or a salt thereof according to claim 1, wherein $R^1$, $R^2$ and $R^3$ independently are an alkyl group having 10 to 22 carbon atoms.

4. The compound or a salt thereof according to claim 1, wherein L represents a divalent bridging group represented by —$(CH_2)_g Y^1 COY^2 (CH_2)_h$— (wherein $Y^1$ and $Y^2$ independently represent single bond, —O—, —NH—, or —NCH$_3$—, provided that $Y^1$ and $Y^2$ do not represent single bond at the same time, g represents an integer of 2 to 20, and h represents an integer of 1 to 4).

5. The compound or a salt thereof according to claim 4, wherein either $Y^1$ or $Y^2$ is single bond.

6. A chelate compound or a salt thereof, which consists of the compound according to claim 1 and a metal ion.

7. The chelate compound or a salt thereof according to claim 6, wherein the metal ion is a metal ion of a paramagnetic element selected from the elements of the atomic numbers 21 to 29, 42, 44, and 57 to 71.

8. A liposome containing the compound or a salt thereof according to claim 6 as a membrane component.

9. The liposome according to claim 8, which contains a phosphatidylcholine and a phosphatidylserine as membrane components.

10. A contrast medium, which comprises the liposome according to claim 8.

11. The contrast medium according to claim 10, which is used for imaging of a vascular disease.

12. The contrast medium according to claim 10, which is used for imaging of vascular smooth muscle cells abnormally proliferating under influence of foam macrophages.

13. The contrast medium according to claim 10, which is used for imaging of a tissue or lesion in which macrophages localize.

14. The contrast medium according to claim 13, wherein the tissue in which macrophages localize is selected from the group consisting of tissues of liver, spleen, air vesicle, lymph node, lymph vessel, and renal epithelium.

15. The contrast medium according to claim 13, wherein the lesion in which macrophages localize is selected from the group consisting of lesions of tumor, inflammation, and infection.

16. A liposome containing the compound or a salt thereof according to claim 1 as a membrane component.

17. A contrast medium, which comprises the liposome according to claim 16.

* * * * *